United States Patent [19]

Garlen et al.

[11] Patent Number: 4,707,354

[45] Date of Patent: Nov. 17, 1987

[54] MATURE SKIN TREATMENT AND PROTECTANT COMPOSITIONS AND METHODS OF USING SAME

[75] Inventors: David Garlen, Roselle Park, N.J.; Hilde R. Koehn; Peter W. Koehn, both of Huntington, N.Y.; J. D. McColl, Chattanooga, Tenn.

[73] Assignee: Alpen Tau, Inc., Huntington, N.Y.

[21] Appl. No.: 8,084

[22] Filed: Jan. 21, 1987

Related U.S. Application Data

[63] Continuation of Ser. No. 745,699, Jun. 17, 1985, abandoned.

[51] Int. Cl.$^4$ .......................... A61K 7/42; A61K 7/44; A61K 9/08; A61K 9/12
[52] U.S. Cl. .......................... 424/47; 424/59; 424/60; 514/458; 514/474; 514/588; 514/725; 514/773; 514/844; 514/847; 514/855; 514/873; 514/937
[58] Field of Search .......................... 424/47, 59, 60; 514/844, 847

[56] References Cited

U.S. PATENT DOCUMENTS

| | | | |
|---|---|---|---|
| 3,305,557 | 2/1967 | Lubowe | 260/299 |
| 3,506,758 | 4/1970 | Epstein et al. | 424/60 |
| 4,098,881 | 7/1978 | Majeti | 424/59 |
| 4,129,645 | 12/1978 | Barnett et al. | 424/60 |
| 4,154,823 | 5/1979 | Schutt et al. | 424/60 |
| 4,193,989 | 3/1980 | Teng et al. | 424/60 |
| 4,264,581 | 4/1981 | Kerkhof et al. | 424/60 |
| 4,284,621 | 8/1981 | Preuss et al. | 424/59 |
| 4,327,078 | 4/1982 | Charlet et al. | 424/59 |
| 4,434,154 | 2/1984 | McShane | 424/60 |
| 4,457,911 | 7/1984 | Conner et al. | 424/59 |
| 4,482,537 | 11/1984 | El-Menshawy et al. | 424/59 |

OTHER PUBLICATIONS

De Navarre, 1941, The Chemistry and Manufacture of Cosmetics, pp. 654 to 656.
Kligman, L. H. et al, Sunscreens Promote Repair of Ultraviolet Radiation-Induced Dermal Damage. J. Invest. Dermatol., 1983, Aug., 81(2):98-102.
Oikarinen, A. et al, Connective Tissue Alternations in Skin Exposed to Natural and Therapeutic UV-Radiation. Photodermatol., 1985, Feb.; 2(1):15-26.
Berger, H. et al, Experimental Elastosis Induced by Chronic Ultraviolet Exposure. Arch. Dermatol. Res. 1980; 269(1):39-49.
Alpermann, H. et al, Effect of Repeated Ultraviolet Radiation on Skin of Hairless Mice, Arch. Dermatol. Res. 1978 Jun. 29; 262(1):15-25.
Lovell, W. W., Ultraviolet Irradiation of Dermal Collagen in Vivo, Trans. St. Johns Hosp. Dermatol. Soc. 1973; 59(2):166-74.
Al-Hajj, G. et al, Effect of Ultraviolet Light on the Skin, W. Va. Med. J. 1973 Dec.; 69(12):351-2.
Raab, W., Effects of Ultraviolet Light on Human Dermal Collagen in Virto, Arch. Klin. Exp. Dermatol. 1969; 234(1): 36-43.
Johnston, K. J. et al, Ultraviolet Radiation-Induced Connective Tissue Changes in the Skin of Hairless Mice, J. Invest. Dermatol. 1984 June; 82(6):587-90.
Sakura, S. et al, Photolysis of Pyridinoline, a Cross--Linking Amino Acid of Collagen, by Ultraviolet Light, Can. J. Biochem. 1982 May; 60(5): 525-9.
Raab, W. P., Changes in Hydroxyproline Content of Human Dermal Collagen Following UV-Irradiation in Nitro., Specialia 1969 Jun. 15; 25(6):624.
Consden, R. et al, Action of Ultraviolet Light on Soluble Collagens, Nature 1967 Jul. 8; 215(7):165.
Bottoms, E. et al, Effect of Ultraviolet Irradiation on Skin Collagen, Nature 1966 Jul. 1; 211(7):97.

*Primary Examiner*—Dale R. Ore
*Attorney, Agent, or Firm*—Martin A. Levitin

[57] ABSTRACT

There are disclosed sunscreen, protectant, moisturizing dermatological compositions and methods for administration of such compositions to human skin in a manner such that a high degree of epidermal, especially stratum corneum, rehydration is attained in conjunction with nearly complete screening of cancer-causing actinic radiation as well as mechanical skin protection.

10 Claims, No Drawings

MATURE SKIN TREATMENT AND PROTECTANT COMPOSITIONS AND METHODS OF USING SAME

This application is a continuation of application Ser. No. 745,699, filed 6-17-85, now abandoned.

FIELD OF THE INVENTION

The present invention relates generally to topical broad-spectrum sunscreen, protectant and moisturizing compositions and methods for utilizing such compositions to protect mature skin from dehydration, irritation and cell damage due to exposure to sunlight, wind, salt water, and other environmental irritants as well as to treat mature skin which has already been damaged by exposure to such irritants.

BACKGROUND OF THE INVENTION

A broad range of liquids, creams, lotions and gels have been proposed for topical application to screen human skin from the burning effects of solar radiation while permitting some portion of the sun's rays to pass through to achieve the effect referred to as tanning. Few, if any, of the compositions heretofore proposed have dealt with the problem that even such tanning solar radiation can have detrimental effects on skin health such as causing the condition called premature aging or inducing actinic-sourced cancer of the skin.

Additionally, few, if any, skin care products have been formulated specifically to address the sun-induced degenerative problems encountered by skin in its maturing cycle. In the dermis, for example, ultraviolet rays produce elastotic degeneration, and a breakdown of elastic fibers that causes a person to appear aged in excess of his or her chronological years.

Nor have products been formulated to address the skin problems created in large numbers of older people by their regimen of daily medication. Some medications are not fully excreted by the body, and over time build up residues in the skin tissues which, when exposed to sunlight, cause phototoxic reactions such as blistering and burns. Drugs which have been reported implicated in photosensitive skin reactions include such commonly prescribed medications as tetracycline antibiotics, phenothiazine derivative tranquilizers, thiazide diuretics, certain antihistamines, certain anticonvulsants, sulfonylurea antidiabetics, estrogens, oral contraceptives and sulfonamides.

It has been thought, heretofore, that ultraviolet damage to the skin was irreversible. Recent research reported in the literature demonstrates, however, that animal skin has intrinsic mechanisms to halt and even reverse dermal damage, once the actinic radiation insult is stopped. Skin care products available in the marketplace have not, for the most part, addressed this need for therapeutic restoration of sun-damaged skin. An effective topical skin preparation should contain moisturizers, humectants, oils, penetrants and other ingredients which will assist the skin in its self-restorative processes.

Modern industrial societies augment nature's climatic and environmental skin irritants such as dry hot winds, salt spray, winter cold and the like. Air pollution, chemicals, heating and air conditioning systems, detergents and household cleaning products dry the skin and damage tissue in a variety of ways. Skin care products, to be properly prophylactic, should contain medically active skin protectants which will act as light weight, nonocclusive mechanical barriers against environmental irritants.

Accordingly, it is an object of this invention to provide compositions which will overcome the shortcomings of prior preparations which did not adequately screen the skin from solar radiation across the spectrum from 290 nanometers through 365 nanometers.

Another object of this invention is to provide compositions which will contain safe and effective protectant and demulcent ingredients to soften, protect and allow nature to repair damaged skin and to stimulate growth of healthy tissue.

Yet another object of this invention is to provide compositions which will contain ingredients to penetrate the skin deeply to deliver the active ingredients and to compensate for the diminished production of sebum in mature or prematurely aged skin.

Still another object of the present invention is to provide compositions for skin treatment which will include cosmetically effective oils, moisturizers and humectants to promote softness, retain moisture, act as emollients and to halt and even reverse dermal damage caused by previous failure to protect the skin from solar radiation and environmental irritants.

A further object of the present invention is to provide compositions of the types described which will not break down over extended periods of time and will have adequate shelf life to permit proper commercial exploitation.

Yet a further object of the present invention is to provide methods for the treatment of human skin to prevet degenerative skin conditions designated as premature aging and to aid in the prevention of actinic-sourced skin cancer.

Other objectives and advantages of the present invention will appear as the specification proceeds.

SUMMARY OF THE INVENTION

This invention relates to dermatological compositions, for topical application to human skin, which provide medical prevention, physical protection and cosmetic restoration properties, containing the sunscreens oxybenzone, ethyl 4-[bis(hydroxypropyl)]aminobenzoate, padimate O and 2-phenylbenzimidazole-5-sulfonic acid, and the skin protectants allantoin and dimethicone, in a cosmetically and therapeutically acceptable carrier or vehicle, containing suitable solvents, moisturizers, humectants, oils, emulsifiers thickeners, thinners, surface active agents, fragrances, preservatives, antioxidants and the like.

DETAILED DESCRIPTION OF THE INVENTION

The compositions of this invention are prepared in any desired manner and in any suitable order or sequence of addition of the various components and those skilled in the art will be readily cognizant of those available mixing procedures which are operative for ease and speed of production of such compositions.

In general, the compositions of the invention typically contain, approximately by weight, 2 to 6% oxybenzone, 1 to 5% ethyl 4-[bis(hydroxypropyl)]aminobenzoate, 1.4 to 8% paidimate O, 1 to 4% 2-phenylbenzimidazole-5-sulfonic acid, 0.5 to 2% allantoin and 1 to 30% dimethicone in a cosmetically and dermatologically acceptable carrier or vehicle. The composition may be provided in the form of a cream, emulsion, lotion, spray, ointment, mousse or foam mask and a layer of such composition should be applied to the skin regularly, preferably daily.

The following Example illustrates compositions of the present invention in the form of a dermatological cream.

| Ingredient | Weight Percent |
| --- | --- |
| oxybenzone | 3 |
| ethyl 4-[bis(hydroxypropyl)] amino benzoate | 2 |
| padimate-O | 7 |
| 2-phenylbenzimidazole-5-sulfonic acid | 2 |
| allantoin | 1 |
| dimethicone | 1.25 |
| deionized water | 44 |
| petrolatum | 5 |
| sodium lactate | 5 |
| glyceryl stearate | <1 |
| stearic acid | 3 |
| cetyl alcohol | 3 |
| sodium PCA | 3.25 |
| urea | 1 |
| PEG-100 stearate | <1 |
| squalane | 1 |
| sesame oil | 1 |
| jojoba oil | 1 |
| sunflower oil | 1 |
| cocoa butter | 1 |
| tocopheryl acetate | <1 |
| triethanolamine | 1 |
| collagen | <1 |
| elastin | <1 |
| silk powder | <1 |
| reticulin | <1 |
| vegetable oil | <1 |
| retinyl palmitate | <1 |
| cholecalciferol | <1 |
| arachidonic acid | <1 |
| linoleic acid | <1 |
| linolenic acid | <1 |
| isopropyl palmitate | <1 |
| cholesterol | <1 |
| adenosine triphosphate | <1 |
| alginic acid | <1 |
| aloe vera gel | <1 |
| alpine rose extract | <1 |
| gentian extract | <1 |
| ascorbic acid | <1 |
| Balm of Gilead | <1 |
| glycerin | <1 |
| biotin | <1 |
| hyaluronic acid | <1 |
| glycine | <1 |
| propylene glycol | <1 |
| proline | <1 |
| hydroxyproline | <1 |
| glucose | <1 |
| chondroitin sulfate | <1 |
| glutamic acid | <1 |
| ribonucleic acid | <1 |
| panthenol | <1 |
| alanine | <1 |
| pyridoxine hydrochloride | <1 |
| oleic acid | <1 |
| arginine | <1 |
| aspartic acid | <1 |
| myristyl myristate | <1 |
| lysine | <1 |
| serine | <1 |
| leucine | <1 |
| valine | <1 |
| threonine | <1 |
| phenylalanine | <1 |
| isoleucine | <1 |
| hydroxylysine | <1 |
| histidine | <1 |
| methionine | <1 |
| tyrosine | <1 |
| cysteine | <1 |
| cystine | <1 |
| fragrance | <1 |
| -continued | |
| Ingredient | Weight Percent |
| diazolidinyl urea | <1 |
| methylparaben | <1 |
| propylparaben | <1 |

The ingredients are combined using known cosmetic and dermatological product manufacturing techniques. The final product is then milled into a colloidal microemulsion by subjecting it to a special milling in a Manton-Gaulin submicron disperser.

When tested in standardized animal tests, the composition of the example proved not to be irritating to the eyes or skin of the test subjects.

The pH of the cream was approximately 5, an appropriate value to avoid disturbing the normal "acid mantle" of human skin and to impart mild antiseptic properties.

When tested on human subjects in combined insult patch tests and photoallergy/phototoxicity testing procedures, the composition of the example did not induce clinically meaningful irritation nor produce evidence of induced allergic contact dermatitis, photoallergy (photosensitization) nor phototoxicity.

The composition of the example produced a mean Sun Protection Factor (SPF) of 19.39 in standardized tests on twenty human subjects.

In transmission spectra tests, 0.5% concentration of the composition of the example in isopropanol showed an excellent block between 280 and 365 nanometers, covering both the UV-B and UV-A ranges. This cream also passed the antimicrobial preservative effectiveness test.

Samples of the composition were subjected to thirty day accelerated stability tests at 45 degrees Centigrade in a variety of product packages. Weight loss was minimal and viscosity and pH changes were within the normal range for acceptable shelf-life.

This invention has been disclosed with respect to a certain preferred embodiment, and it will be understood that modifications and variations thereof obvious to those skilled in the art are to be included within the spirit and purview of this application and the scope of the appended claims.

What is claimed is:

1. A sunscreen, protectant, moisturizing, non-toxic dermatological composition comprising, approximately by weight, 2 to 6% oxybenzone, 1 to 5% ethyl 4-[bis(-hydroxypropyl)]aminobenzoate, 1.4 to 8% padimate O, 1 to 4% 2-phenylbenzimidazole-5-sulfonic acid, 0.5 to 2% allantoin and 1 to 30% dimethicone in a cosmetically and dermatologically acceptable carrier or vehicle.

2. A composition according to claim 1 in the form of a cream, emulsion, lotion, spray, ointment, mousse or foam mask.

3. The composition of claim 1, wherein said carrier or vehicle contains a member selected from the group consisting of solvents, moisturizers, humectants, oils, emulsifiers, thickeners, surface active agents, fragrances, preservatives and antioxidants.

4. A sunscreen, protectant, moisturizing, non-toxic dermatological composition comprising a cosmetically and dermatologically acceptable carrier containing, by weight, 3% of oxybenzone, 2% of ethyl 4-[bis(hydroxypropyl)]aminobenzoate, 7% of padimate O, 2% of 2- phenylbenzimidazole-5-sulfonic acid, 1% of allantoin and 1.25% of dimethicone.

5. A sunscreen, protectant, moisturizing, dermatological composition consisting essentially of the formulation:

| | |
|---|---|
| oxybenzone | 3% |
| ethyl 4-[bis(hydroxypropyl)] aminobenzoate | 2 |
| padimate O | 7 |
| 2-phenylbenzimidazole-5-sulfonic acid | 2 |
| allantoin | 1 |
| dimethicone | 1.25 |
| deionized water | 44 |
| petrolatum | 5 |
| sodium lactate | 5 |
| glyceryl stearate | <1 |
| stearic acid | 3 |
| cetyl alcohol | 3 |
| sodium PCA | 3.25 |
| urea | 1 |
| PEG-100 stearate | <1 |
| squalane | 1 |
| sesame oil | 1 |
| jojoba oil | 1 |
| sunflower oil | 1 |
| cocoa butter | 1 |
| tocopheryl acetate | <1 |
| triethanolamine | 1 |
| collagen | <1 |
| elastin | <1 |
| silk powder | <1 |
| reticulin | <1 |
| vegetable oil | <1 |
| retinyl palmitate | <1 |
| cholecalciferol | <1 |
| arachidonic acid | <1 |
| linoleic acid | <1 |
| linolenic acid | <1 |
| isopropyl palmitate | <1 |
| cholesterol | <1 |
| adenosine triphosphate | <1 |
| alginic acid | <1 |
| aloe vera gel | <1 |
| alpine rose extract | <1 |
| gentian extract | <1 |
| ascorbic acid | <1 |
| Balm of Gilead | <1 |
| glycerin | <1 |
| biotin | <1 |
| hyaluronic acid | <1 |
| glycine | <1 |
| -continued | |
| propylene glycol | <1 |
| proline | <1 |
| hydroxyproline | <1 |
| glucose | <1 |
| chondroitin sulfate | <1 |
| glutamic acid | <1 |
| ribonucleic acid | <1 |
| panthenol | <1 |
| alanine | <1 |
| pyridoxine hydrochloride | <1 |
| oleic acid | <1 |
| arginine | <1 |
| aspartic acid | <1 |
| myristyl myristate | <1 |
| lysine | <1% |
| serine | <1 |
| leucine | <1 |
| valine | <1 |
| threonine | <1 |
| phenylalanine | <1 |
| isoleucine | <1 |
| hydroxylysine | <1 |
| histidine | <1 |
| methionine | <1 |
| tyrosine | <1 |
| cysteine | <1 |
| cystine | <1 |
| fragrance | <1 |
| diazolidinyl urea | <1 |
| methylparaben | <1 |
| propylparaben | <1 |

6. A method for treating (the prevention of premature aging of) skin comprising covering said skin (at least daily) with a layer of the composition as defined in claim 1.

7. A method for treating skin comprising covering said skin with a layer of a composition as defined in claim 2.

8. A method for treating skin comprising covering said skin with a layer of a composition as defined in claim 5.

9. A method for treating skin comprising covering said skin with a layer of the composition as defined in claim 3.

10. A method for treating skin comprising covering said skin with a layer of a composition as defined in claim 4.

* * * * *